(12) United States Patent
Horppu et al.

(10) Patent No.: US 6,387,074 B1
(45) Date of Patent: May 14, 2002

(54) TWO-CHAMBER DRUG DELIVERY DEVICE COMPRISING A SEPARATING MEMBRANE

(75) Inventors: Petri Horppu, Göteborg (SE); Jörgen Friis, Tommerup (DK)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/011,729

(22) PCT Filed: Nov. 10, 1997

(86) PCT No.: PCT/SE97/01876

§ 371 Date: Feb. 17, 1998

§ 102(e) Date: Feb. 17, 1998

(87) PCT Pub. No.: WO98/20921

PCT Pub. Date: May 22, 1998

(30) Foreign Application Priority Data

Nov. 13, 1996 (SE) ............................................... 9604162

(51) Int. Cl.[7] ........................ A61M 37/00; B65D 25/08
(52) U.S. Cl. .......................... 604/89; 604/181; 604/82; 206/221
(58) Field of Search ........................... 604/82, 403–416, 604/83, 85, 87, 89, 181–187, 190–91, 518–520, 164.01, 167.01–167.04; 206/219–222, 363–366

(56) References Cited

U.S. PATENT DOCUMENTS

| | | | |
|---|---|---|---|
| 3,756,390 A | * 9/1973 | Abbey et al. | 206/47 |
| 4,376,799 A | 3/1983 | Tusim | 428/213 |
| 4,437,858 A | 3/1984 | Ty et al. | 604/90 |
| 4,636,412 A | 1/1987 | Field | 428/35 |
| 4,983,164 A | 1/1991 | Hook et al. | 604/87 |
| 5,944,709 A | * 8/1999 | Barney et al. | 604/410 |
| 5,947,287 A | * 9/1999 | Weiss et al. | 206/439 |

* cited by examiner

Primary Examiner—Jeffrey R. Jastrzab
Assistant Examiner—Patricia Bianco
(74) Attorney, Agent, or Firm—White & Case LLP

(57) ABSTRACT

A drug delivery device for delivery of a drug which comprises a mixture of a first substance and a second substance, the device including a first chamber (24) for housing the first substance, a second chamber (30) for housing the second substance and a membrane (28) which on application of a predetermined condition thereto is movable from a first disposition in which it partitions the first and second chambers to prevent mixture of the first and second substances to a second disposition in which it enables the first and second substances to be mixed. In one aspect, the membrane (28) contains a barrier material comprising polychlorotrifluoroethylene or a copolymer thereof, polyvinylidene chloride or a copolymer thereof or a silicon oxide. In another aspect, the first chamber (24) is formed from a polyethylene based polymer.

14 Claims, 5 Drawing Sheets

TWO-CHAMBER DRUG DELIVERY DEVICE COMPRISING A SEPARATING MEMBRANE

BACKGROUND

The present invention relates to a membrane and a chamber of a drug delivery device which is for delivery of a drug comprising a mixture of first and second substances and which includes the chamber for housing the first substance, another chamber for housing the second substance and the membrane for partitioning the first chamber from the second chamber to prevent mixture of the first and second substances until the device is activated. The invention further relates to a drug delivery device of the aforementioned type, one example of which being an automatic injector.

There are certain instances when a person will need to inject a drug solution at a time which cannot be predicted, for example soldiers in the field who have been subject to a nerve gas attack. It is therefore important that such a person be provided with an injector which can be handled and activated in a simple and quick manner and which is reliable. Automatic injectors have therefore been developed in response to this need.

Automatic injectors will invariably be stored for many years prior to use and preferably such storage should be able to be at elevated temperatures up to 40° C., that is to say, there should be no need for cold storage under normal conditions (normal ambient temperatures, body temperatures). Automatic injectors will also often be subjected to hard conditions during the period when potential users carry them. The shelf-life of automatic injectors is therefore equally important With this in mind, the stability of drug solutions may deteriorate when stored for long periods. This is the case for certain nerve gas antidotes which are stable in powder form but which prove difficult to stabilise in solution for long storage periods.

There is thus a demand for an automatic injector for delivery of a drug solution which is simple, quick and reliable, in which it is possible to store the components which when mixed form the drug solution separately for a long period and in which means are provided which on activation of the injector causes the components to be mixed easily for injection of the drug solution.

An automatic injector which meets this requirement is made known in EP-A-288443.

EP-A-288443 makes known an automatic injector for delivery of a drug solution comprising a mixture of first and second substances, the device having a first chamber which contains the first substance, a second chamber which contains the second substance and a membrane which on activation of the injector moves from a first disposition in which it partitions the first and second chambers to prevent mixture of the first and second substances to a second disposition in which it enables the first and second substances to be mixed for injection thereof.

It will be apparent that the construction of the membrane needs to be such as to prevent premature mixing of the first and second substances. The membrane must therefore present a barrier against migration of the first and second substances therethrough. The membrane should also (i) be relatively easy to manufacture, (ii) not absorb substances from the substances in the chambers nor emit substances to those substances, and (iii) meet high standards in regard of gas permeability and radiation, e.g. should be able to withstand the normal radiations used for sterilisation, for example gamma and lambda radiation.

The automatic injector of EP-A-288443 is described with reference to its use for delivery of a drug solution formed on mixing of a powder with a liquid, as needed for the nerve gas antidotes of the type mentioned hereinabove which are stable in powder form but not stable for long periods when in solution. One of the chambers of the injector thus houses the powder (hereinafter the "powder chamber") while the other chamber houses a liquid for the powder to be mixed with (hereinafter the "liquid chamber"). As mentioned above, it should be possible to store the injector for long periods and preferably at an elevated temperature. This means that the long-term and short-term requirements regarding the impermeability of the membrane to the liquid and liquid vapour has to be very strict.

In most cases the liquid for mixing with the powder will be water-based. With this in mind, it is previously known to use a membrane which contains aluminium as a barrier material to water and water vapour, as for example in the automatic injector of EP-A-288443.

In certain instances it may be that the pH of the substances in the chambers needs adjusting for stabilising purposes, this being particularly so for storage at elevated temperatures. This can have an adverse effect on the long-term integrity of the membrane. Furthermore, one of the substances may be chemically aggressive per se with respect to the material/materials of the membrane and thus also have an impact on the long-term integrity of the membrane, a condition being aggravated at elevated temperatures.

This is the case where the automatic injector of EP-A-288443 is to deliver a nerve gas antidote with the powder chamber of the injector containing HI-6 powder and the liquid chamber housing a mixture of Atropine and Avizaphone. In this instance, the pH of the Avizaphone/Atropine mixture is adjusted to a low pH value of pH 4 to increase the stability of the Atropine. This low pH value, however, has a deleterious effect over time on the aluminium contained in the membrane. Moreover, Avizaphone is chemically aggressive with respect to aluminium. The shelf-life of the automatic injector is thus handicapped by the poor resistance of the aluminium barrier material to the properties of the Atropine/Avizaphone liquid mixture.

There is thus a need for a membrane separating the liquid and powder chambers in this automatic injector which has improved resistance against the liquid mixture in addition to presenting a barrier against liquid or liquid vapour permeating into the powder chamber from the liquid chamber and adversely affecting the powder, for example by causing the powder to recrystallise and hence decrease the solubility of the powder or otherwise deteriorate the powder.

In the automatic injector of EP-A-288443 the membrane in its first disposition is welded across the powder chamber to close off the powder chamber and separate the contents of the powder chamber from the contents of the liquid chamber. A piston then acts on the powder in the powder chamber on activation of the injector to build up sufficient hydraulic pressure to bring the membrane to the second disposition by rupture thereof A recent development to the injector, though, has seen the piston being provided with a leading edge which on activation of the injector causes the membrane to be brought to the second disposition by peeling of the membrane off the powder chamber This has the advantage that the membrane can be made stronger. On the other hand, though, this places certain requirements on the weld formed between the membrane and the powder chamber.

With this in mind, it has been previously proposed to form the powder chamber from polypropylene with the membrane having a laminate construction comprising a layer of aluminium on one of the major surfaces of which a layer of welding material is adhered for welding the membrane to the powder chamber. The use of polypropylene to form the powder chamber, however, gives rise to difficulties in finding a material suitable for welding the membrane to the powder chamber. The welding materials either form a weld joint which is too weak thereby compromising the shelf-life of the injector or a weld joint that is too strong thereby compromising the ability of the membrane to be easily displaced to the second disposition on activation of the injector by peeling off.

There is thus also the need for a powder chamber which presents a surface to which it is easier to weld the membrane.

The present invention therefore proposes to satisfy these needs. It is to be pointed out, however, that the invention has application to the general field of devices which are for delivering a drug comprising a mixture of substances and which are provided with chambers for separately housing the substances until such time as the device needs to be used whereupon the substances are mixed for delivery of the drug by the device, that is to say, the invention is not restricted to the case of automatic injectors of the type hereinabove described.

SUMMARY OF THE INVENTION

According to a first aspect of the present invention there is provided a membrane for partitioning first and second chambers in a drug delivery device for delivery of a drug comprising a mixture of first and second substances, the first and second chambers respectively being for housing the first and second substances, characterised in that the membrane comprises a barrier material comprising polychlorotrifluoroethylene or a copolymer thereof, polyvinylidene chloride or a copolymer thereof or a silicon oxide. These barrier materials have a greater resistance to the corrosive environments that afflict the previously proposed barrier material of aluminium.

According to a second aspect of the present invention there is provided a drug delivery device for delivery of a drug which comprises a mixture of a first substance and a second substance, the device including a first chamber for housing the first substance, a second chamber for housing the second substance and a membrane which on application of a predetermined condition thereto is movable from a first disposition in which it partitions the first and second chambers to prevent mixture of the first and second substances to a second disposition in which it enables the first and second substances to be mixed characterised in that the membrane comprises a barrier material comprising polychlorotrifluoroethylene or a copolymer thereof, polyvinylidene chloride or a copolymer thereof or a silicon oxide.

The term "drug delivery device" is to be taken as covering not only a complete device but also a cartridge, ampoule or the like which includes the partitioned first and second chambers and which is separable from the complete device.

It will be appreciated that the drug delivery device of the invention may be for delivery of a drug which is formed from more than just a mixture of first and second substances. In this case, the drug delivery device of the invention may include further chambers for separately housing the additional substances which together with the first and second substances will form the drug.

In an embodiment of the invention hereinafter to be described the membrane is a laminate structure composed of a plurality of layers and the barrier material is contained in at least one layer of the laminate structure.

In an embodiment of the invention hereinafter to be described the laminate structure includes an outer layer of a material which enables the laminate structure to be welded to the first chamber to close the first chamber off and thereby partition the first and second chambers. Preferably, the outer layer is formed of a material which when welded to the first chamber results in a weld joint which enables the membrane to be brought to its second disposition by peeling of the membrane off the first chamber. Amongst other things, this allows the strength of the membrane to be greater than in the case where the membrane is to be brought to the second disposition by rupture thereof.

In an embodiment of the invention the outer layer is formed from a polyethylene or cellulose based polymer and the first chamber is formed of polypropylene or a copolymer thereof or of a polyethylene based polymer. Where polyethylene based polymers form the outer welding layer and the first chamber there may be mentioned blends of polyethylene with ethylene-vinyl acetate (EVA), ethylene-butylacrylate (EBA), polybutylene (PB) or butyl acrylate (BA), cross-linked polyethylenes and polyethylene ionomers as the material for the outer welding layer and polyethylene or high density polyethylene for the material of the first chamber. Alternatively, the outer layer can be formed of polypropylene, for instance a polypropylene lacquer, or a blend of polypropylene and butyl acrylate and the first chamber is of polypropylene or a copolymer thereof.

In an embodiment of the invention hereinafter to be described the barrier material is contained in a barrier layer of the laminate structure and the laminate structure includes a layer of a polyester material, for example polyethylene terephthalate, which is mounted to one of the major surfaces of the barrier layer such that the polyester layer spaces the barrier layer from the outer layer.

For ease of manufacture of the membrane and mounting thereof in certain drug delivery devices the polyester layer is a first polyester layer and the laminate structure further includes a second layer of a polyester material, for example of polyethylene terephthalate, which is mounted to the major surface of the barrier layer opposite to that on which the first polyester layer is mounted.

Where the barrier material is silicon oxide it may be useful for the silicon oxide to be supported in a matrix material, for example in a matrix of polyethylene terephthalate, as is sold by Mitsubishi under the brand name Techbarrier-S. The silicon oxide may be silicon dioxide.

According to a third aspect of the present invention there is provided the use of polychlorotrifluoroethylene or a copolymer thereof, polyvinylidene chloride or a copolymer thereof or a silicon oxide in the manufacture of a membrane for positioning in a drug delivery device for delivery of a drug comprising a mixture of first and second substances such that the membrane partitions a pair of chambers in the device which respectively house the first and second substances until the device is activated.

According to a fourth aspect of the present invention there is provided a drug delivery device for delivery of a drug comprising a mixture of first and second substances, the device having a first chamber for housing the first substance, a second chamber for housing the second substance and a membrane which on application of a predetermined condition thereto is movable from a first disposition in which it partitions the first and second chambers to prevent mixture of the first and second substances to a second disposition in which it enables the first and second substances to be mixed, wherein in the first disposition an outer surface of the membrane is welded to a surface of the first chamber characterised in that at least the surface of the first chamber to which the outer surface of the membrane is welded is presented by a polyethylene based polymer. The use of a polyethylene based polymer for forming the welding surface of the first chamber provides greater variety of welding materials that can be used to present the outer surface of the membrane and which form a satisfactory weld joint with the first chamber, i.e. not too strong and not too weak. As examples, polyethylene or cellulose based polymers may be used to present the outer surface of the membrane.

According to a fifth aspect of the present invention there is provided a chamber for a drug delivery device which is for delivery of a drug comprising a mixture of first and second substances and which in an assembled non-activated state will include the chamber as a first chamber for housing the first substance, a second chamber for housing the second substance and a membrane welded across the first chamber to partition the first chamber from the second chamber and thereby prevent mixture of the first and second substances until the device is activated characterised in that the surface of the first chamber to which the membrane is welded in the assembled non-activated state of the device is presented by a polyethylene based polymer.

According to a sixth aspect of the present invention there is provided the use of a polyethylene based polymer in the manufacture of a first chamber of a drug delivery device which is for delivery of a drug comprising a mixture of first and second substances and which includes the first chamber for housing the first substance, a second chamber for housing the second substance and a membrane movable on application of a predetermined condition thereto from a first disposition in which it is welded across the first chamber to partition the first chamber from the second chamber and thereby prevent mixture of the first and second substances to a second disposition in which it enables the first and second substances to be mixed for delivery of the drug by the device.

In an embodiment of the invention according to its fourth, fifth and sixth aspects the polyethylene based polymer is polyethylene or high density polyethylene.

By way of example, a two-chamber automatic injector in accordance with the present invention will now be described with reference to the accompanying Figures of drawings in which:

DETAILED DESCRIPTION OF THE INVENTION

Figure 1:
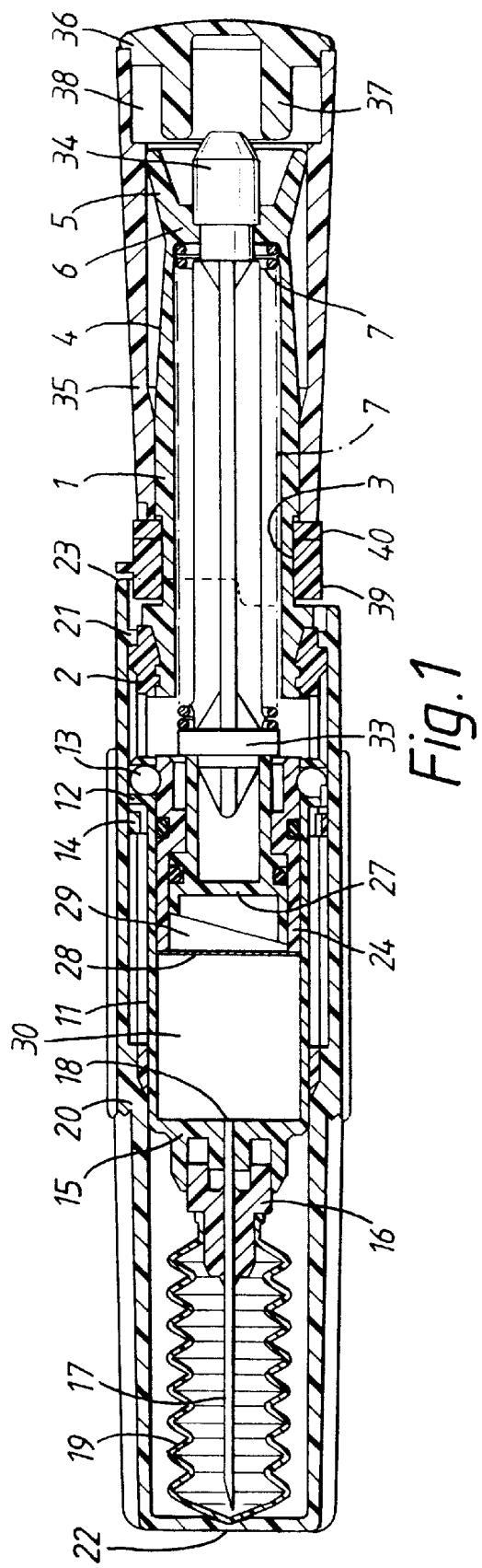
FIG. 1 is a longitudinal sectional view of the injector prior to use.
Figure 2B:
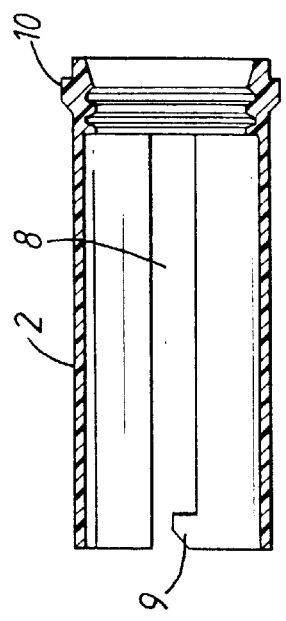
FIG. 2B is a longitudinal sectional view of the guide sleeve.
Figure 2A:
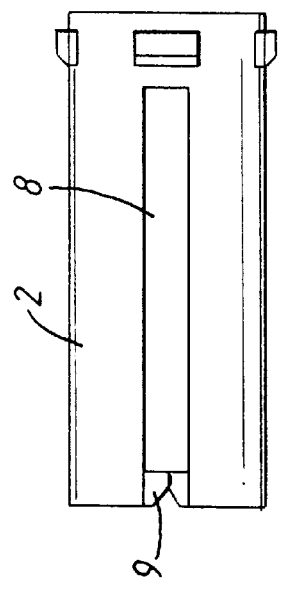
FIG. 2A is a side view of a guide sleeve in the injector.

The injector shown in the Figures comprises a body which consists of a locking sleeve (1) and a guide sleeve (2) which is threaded to the locking sleeve (1). As shown in FIG. 1, the locking sleeve (1) comprises an annular groove (3) and is further split into a number of resilient longitudinal arms (4), preferably four, which at their free ends form diverging tongues (5). Interior of the free ends of the arms (4) radial flange portions (6) are provided which form a seat for a spring (7) mounted inside the locking sleeve (1). As shown in FIGS. 2A and 2B, the guide sleeve (2) comprises two diametrically opposed running grooves (8) extending outside the area of the threaded part, the running grooves ending with stop lugs (9). The other end of the guide sleeve (2) is provided with a number of external pins (1 ).

Figure 3A:
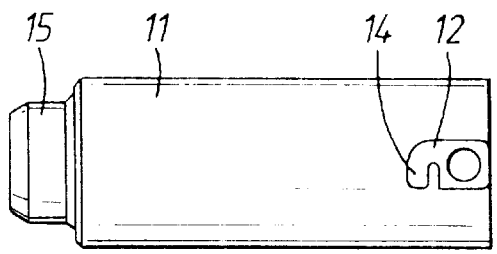
FIG. 3A is a side view of a barrel in the injector.
Figure 3B:
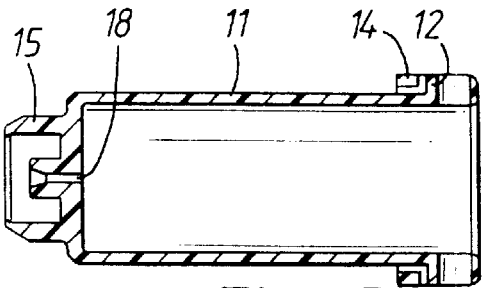
FIG. 3B is a longitudinal sectional view of the barrel.
Figure 4:
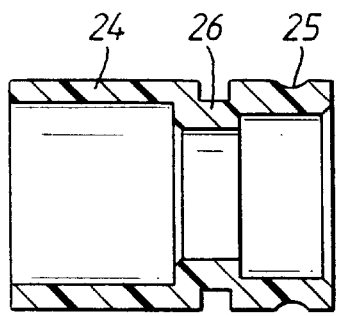
FIG. 4 is an enlarged view of a powder chamber in the injector.

As shown in FIGS. 1, 3A and 3B, a barrel (11) is slidable in the guide sleeve (2) by means of two sliding lugs (12) which are positioned externally and diametrically opposed on the barrel and run in the running grooves (8) of the guide sleeve. The sliding lug (12) comprises a through hole for enclosure of a ball (13) and further comprises a resilient tongue (14). The barrel (11) is sealed at a front end to form a receiving portion (15) in which a needle holder (16 ) with a hollow injection needle (17) is slidable. The receiving portion (15 ) has a centrally placed aperture into which the rear part of the injection needle is (17) is inserted and in whose bottom a piercable membrane (18) is arranged. The front part of the injection needle (17) is enclosed by a protective bellows (19) in order to keep the injection needle sterile.

Figure 6A:
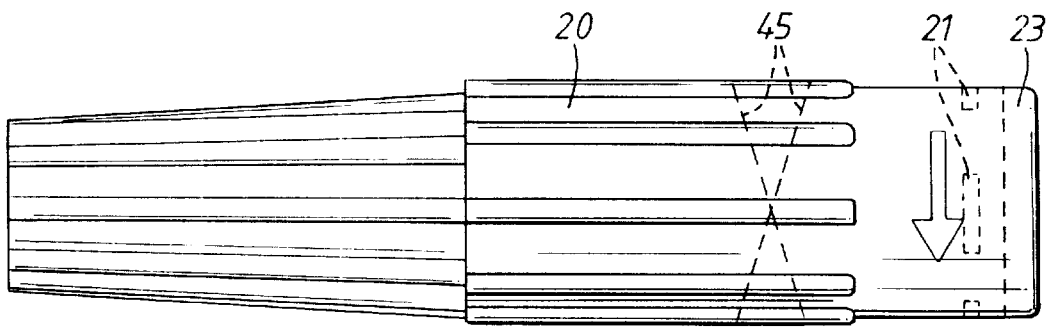
FIG. 6A is a side view of a front cover of the injector.
Figure 6B:
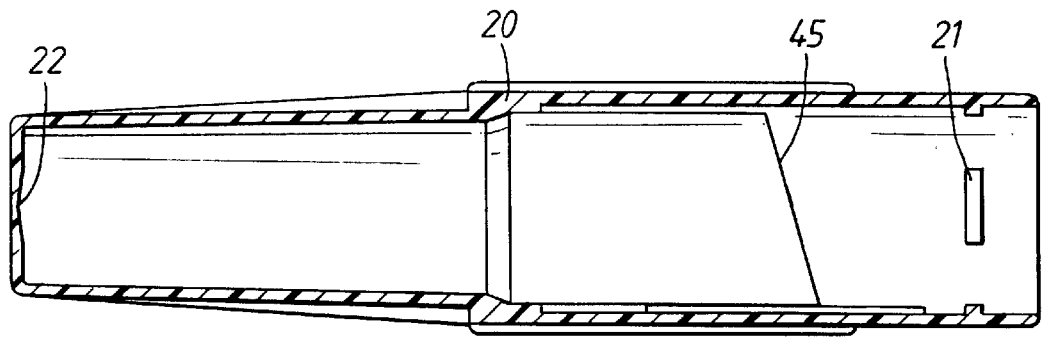
FIG. 6B is a longitudinal sectional view of the front cover.

As shown in FIGS. 1, 6A and 6B, the barrel (11) with the injection needle (17) and the guide sleeve (2) are surrounded by a front cover (20) which is rotatable on the guide sleeve (2). The front cover (20) is provided with external ribs in order to ensure a safe grip on the cover. A number of internal locking lugs (21) are adapted for interaction with the pins (10) of the guide sleeve (2). The front cover (20) is closed at its front end with the front end having a central part (22) of reduced wall thickness. At the rear end of the front cover (20) a prolonged part (23) is formed on about half the circumference of the cover. The part of the front cover (20) which surrounds the guide sleeve (2) has two internal slide-ways (45) being displaced 180° in relation to each other and arranged for interaction with the sliding lugs (12) of the barrel (11). A number of additional grooves are arranged in this part of the front cover (20) as will described in more detail hereinbelow.

Referring now to FIGS. 1, 3A, 3B and 4, at the opposite end of the barrel (11) to the receiving portion (15) a powder chamber (24) made of polyethylene, high density polyethylene or polypropylene is arranged. The envelope surface of the powder chamber (24) is provided with a circumferential external groove (25) to receive the balls (13) of the sliding lug (12) of the barrel (11). An additional annular groove is arranged for a sealing. An internal bead (26) forms a seat for a plunger (27) which is displaceable in the powder chamber (24) to a limited extent, the plunger being provided with a sealing against the inner surface of the powder chamber at one end. A membrane (28) is welded at the inner end of the powder chamber (24) to define a sealed enclosure (29) together with the plunger (27) for containing a powder such as HI-6. In the barrel (11) a liquid chamber (30) is formed on the other side of the membrane (28) for containing a liquid with which the powder is to be mixed, for instance a mixture of Avizaphone and Atropine adjusted to pH 4 where the powder is HI-6.

Figure 10:
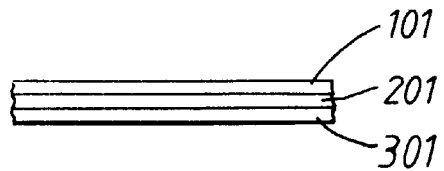
FIG. 10 is a view of a membrane in the injector which is of a laminate structure.

As shown in FIG. 10, the membrane (28) is a laminate structure composed of two outer layers (101, 301) mounted on opposing surfaces of an intermediate layer (201). The outer layer (301) of the membrane which faces the liquid chamber (30) is made of a thin layer of polychlorotrifluoroethylene which acts as a barrier to liquid and liquid vapour from the liquid compartment migrating into the powder chamber and adversely affecting the powder. Use of polychlorotrifluoroethylene as the barrier material in the membrane construction has the advantage over the previously proposed membrane barrier materials such as aluminium that in addition to the impermeability requirements being met polychlorotrifluoroethylene also provides the membrane with improved chemical resistance against an acid environment such as a pH adjusted mixture of Avizaphone and Atropine and against chemically aggressive substances such as Avizaphone.

The outer layer (101) facing the powder chamber (24), on the other hand, is made of a material which can be welded to the powder chamber and thereby allow the membrane (28) to be attached to the powder chamber (24). When the powder chamber (24) is made of polyethylene or high density polyethylene the welding layer of the membrane (28) is ideally formed from a polyethylene based material, preferably one which is not exactly the same as the material of the powder chamber (24), or a cellulose based polymer. As examples of suitable polyethylene based polymers there may be mentionediomo- and copolymers of polyethylene, blends of polyethylene such as polyethylene blended with butyl acrylate, cross-linked polyethylenes and polyethylene ionomers such as Surlyn® A blend of Surlyn® and Bynel® could also be used. These may be applied to the intermediate layer (201) in film form. When the powder chamber (24) is made from polypropylene, though, the welding layer is ideally formed from a polypropylene lacquer, high density polyethylene or a cellulose based polymer.

With regard to the intermediate layer (201) of the laminate structure of the membrane (28), this serves as a reinforcement layer and also the means of presenting the outer layers (101, 301) with a surface having good adhesive properties together with a suitable binder for the outer layers to be bonded to. For both of the membrane constructions mentioned above, polyethylene terephthalate has been found suitable for forming the intermediate layer (201). Other polyesters could be substituted, however, as would be apparent to a skilled reader in the art.

The membrane (28) is manufactured and mounted to the powder chamber (24) by firstly punching out a circular blank from a strip or sheet of the laminate construction, secondly applying the blank onto the periphery of the circular end surface of the powder chamber (24) such that the welding layer (101) faces the end surface of the powder chamber (24) and then finally welding the welding layer to the end surface of the powder chamber (24). To assist in this process, polyethylene terephthalate may also be applied on the outer surface of the polychlorotrifluoroethylene so that the surface and the tools will not become sticky during the manufacture of the laminate construction or the welding thereof to the powder chamber (24) as a result of the melting point of polyethylene terephthalate being higher than the melting point of polychlorotrifluoroethylene.

Figure 5:
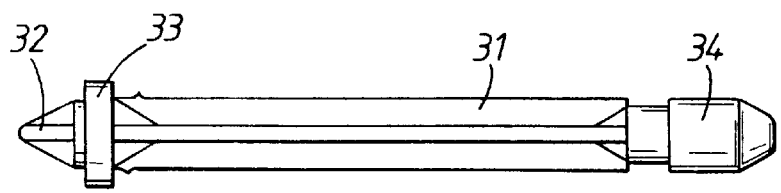
FIG. 5 is a side view of a spring carrier in the injector.

Referring to FIGS. 1 and 5, the plunger (27) bears with its non-sealed, open end on a contact ring (33) at the front end of a spring carrier (31). The spring carrier (31) comprises a cone-shaped centring portion (32) arranged on the contact ring (33) which is inserted into the open end of the plunger (27). The rear end of the spring carrier has a locking head (34) and a flanged middle part extends between the front and rear ends. The locking head (34) interacts with locking lugs in the flange parts (6) on the arms (4) of the locking sleeve (1) for a compression of the spring (7) arranged around the spring carrier (31) between the flange parts (6) and the contact ring (33).

As is shown in FIG. 1, the locking sleeve (1) is surrounded by a displaceable rearward cover (35) which extends up to the edge of the annular groove (3) of the locking sleeve. The rear end of the rearward cover (35) is closed by an activating knob (36) having a cylindrical guiding flange (37) which extends into the rearward cover. The rearward cover is widened internally in the area of the cylindrical guiding flange (37) in order to form a circumferential internal guiding channel (38) at the extreme end of the rearward cover.

Remaining with FIG. 1, a resilient safety ring (39) is arranged in the cylindrical groove (3) of the locking sleeve (1) between the rearward cover (35) and the front cover (20) with the ring having a circumferential extent of about 220. A thin ring (40) is arranged in the groove (3) alongside the safety ring (39) with the safety ring being interconnected by means of a loose loop (not shown), the purpose of which being to keep the safety ring with the injector even after it has been detached from the groove (3).

The activation process of the two-chamber injector comprises two steps, namely a mixing step and a releasing and injecting step. These steps win now be described with reference to FIGS. 7A–7D which show parts of the injector in different phases of the activation process.

Figure 7A:
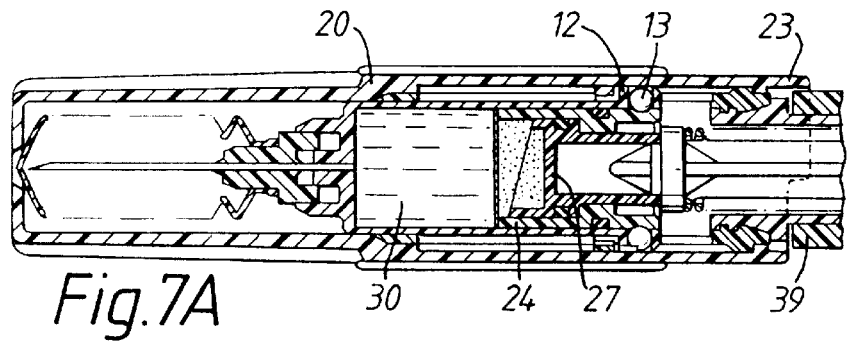
FIG. 7A shows a part of the injector during a starting phase of the activation process of the injector.

FIG. 7A shows the injector in its initial position in which it contains a liquid in the liquid chamber (30) separated from a powder in the powder chamber (24) by the membrane (28). In the initial position the prolonged part (23) of the front cover (20) covers the safety ring (39) in a way that makes it impossible to release the safety ring prematurely. In order to mix the liquid and powder the front cover (20) is rotated, whereby the sliding lugs (12) of the barrel (11) slide on the oblique slide-ways (45) in the front cover (20), thus being pressed rearwards in the running grooves (8) in the guide sleeve (2). The balls (13) and the lugs (12) are pressed against the circumferential grooves (25) of the powder chamber (24) by the inner surface of the front cover (20), which results in both the barrel (11) and the powder chamber (24) being displaced backwards together with the sliding lugs (12). The powder chamber (24) is thereby displaced towards the plunger (27) whereby the leading end of the plunger acts on an edge of the membrane (28).

The material of the welding layer (101) of the membrane (28) and of the powder chamber (24) is selected such that the welding joint formed between them enables the membrane to be peeled away from the powder chamber by the action of the plunger (27) thereon.

Figure 7B:
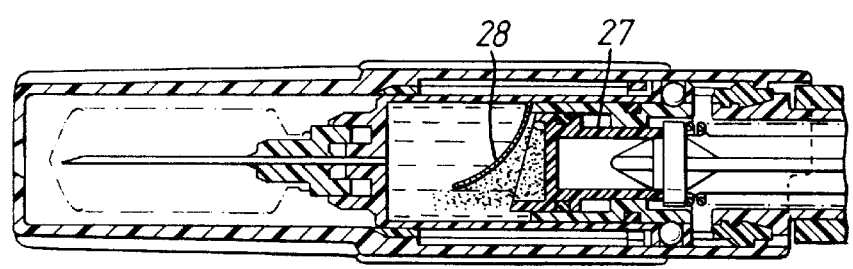
FIG. 7B shows a part of the injector during a mixing phase of the activation process of the injector.

FIG. 7B shows a position where the membrane (28) has been peeled away and the powder is pressed out of the powder chamber (24) to be mixed with the liquid. When the sliding lug (12) reaches the end of the oblique slide-way (45)

the whole cartridge (11, 16, 17) and the powder chamber (24) are moved back to a position where the end surfaces of the plunger (27) and the powder chamber (24) are located in a common plane and the contact ring (33) of the spring carrier bears on the internal bead (26) of the powder chamber. The mixing phase is now completed but can be complemented, if need be, by agitation of the injector.

Figure 9:
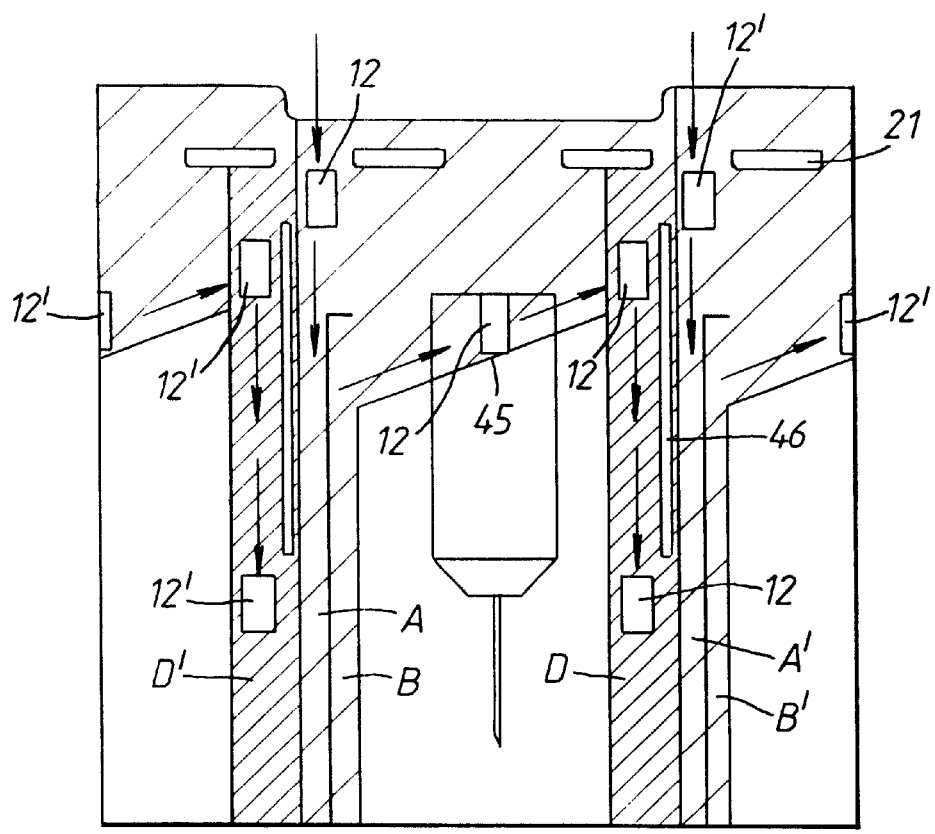
FIG. 9 is a schematic view showing the inner surface of the front cover of the injector with the cover having been slit and unfolded in the plane of the paper.

After the mixing phase the front cover (20) is in such a relative position of rotation that the prolonged part (23) in the outer end covers the opening of the safety ring (39) at the same time as the sliding lugs (12) are located in longitudinal grooves (D, D') in the front cover, as shown in FIG. 9, the grooves (D, D') permitting the balls (13) to be freed from the circumferential grooves (25) of the powder chamber (24). The injector is now ready for a triggering and injection phase which is stared by disengaging the safety ring (39) from the cylindrical groove (3) of the locking sleeve (1) after which the injector is placed against the part of the body into which the injection is to take place.

Figure 8:
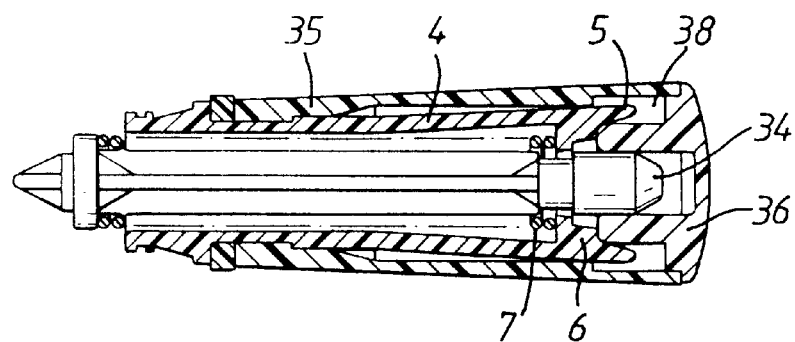
FIG. 8 is a longitudinal sectional view of a rearward cover of the injector in a position when the spring is released.

At this time, the activating knob (36) and the rearward cover (35) are pressed and displaced towards the front cover (20). This is now possible since the safety ring (39) is disengaged. The displacement of the rearward cover relative to the backing sleeve win achieve a release of the spring (7) as shown in FIG. 8. The diverging tongues (5) of the locking sleeve (1) are guided into the guiding channel (38), whereby the flange parts (6) of the resilient arms (4) diverge and the locking head (34) of the spring carrier, as well as the spring (7), are released.

Figure 7C:
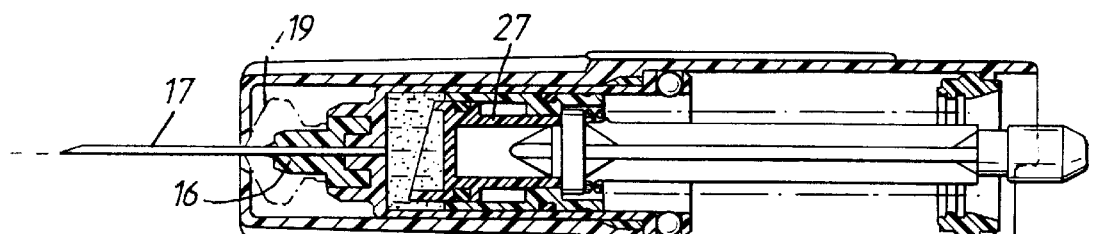
FIG. 7C shows a part of the injector during an injection phase of the activation process of the injector.

FIG. 7C shows the injector in a position in which the injection has stared. The spring (7) presses the powder chamber (24) and the plunger (27) forward together. Since the balls (13) and the lugs (12) can now be forced up into the grooves (D, D') in the front cover, the powder chamber is released from the barrel (11). The plunger (27) presses against the liquid which transmits the pressure hydraulically to the barrel (11) which is driven forwards, by which means the injection needle (17) penetrates the thin material of the central part (22) of the front cover (20). When the protective bellows (19) is compressed, the needle holder (16) is pushed into the receiving portion (15) and the rear point of the injection needle (17) penetrates the membrane (18). In this position a connection between the mixed solution and the injection needle (17) is obtained and the injection starts and continues during the common forward movement of the powder chamber (24) and the plunger (27).

Figure 7D:
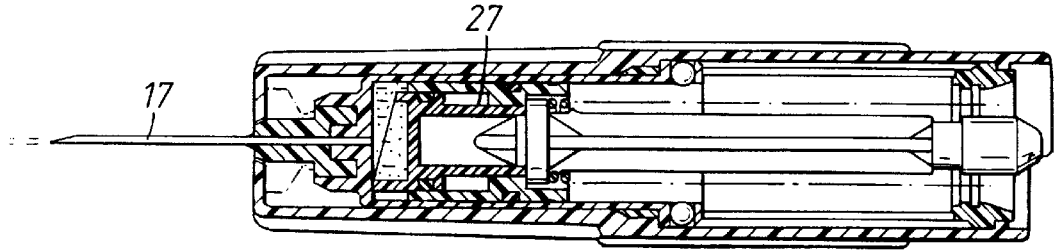
FIG. 7D shows a part of the injector after activation thereof.

FIG. 7D shows the position when the injection is finished and the barrel (11), the powder chamber (24) and the plunger (27) have all been displaced to their respective end positions under the influence of the spring (7) and the mixed solution has been injected into the patient.

FIG. 9 is a schematic view showing the inner surface of the front cover (20) and the way of the sliding lugs (12, 12') along the inner surface when the front cover is rotated. When the front cover is mounted it is guided over the guide sleeve (2) in such a way that the sliding lug (12) (corresponding to the second lug 12' with 180° displacement) is moved along a groove (A) and the locking lugs (21) pass between the pins (10). All grooves are formed with a sharp edge in "the direction of non-rotation" for interaction with the resilient tongue (14) of the sliding lug (12) which falls in behind the sharp edge and thereby prevents a rotation of the front cover (20) in the wrong direction. Subsequently, the front cover (20) is rotated one step further until the sliding lug (12) reaches another groove (B). Groove (3) constitutes the starting position for the activation process of the injector. If the front cover is rotated, the sliding lug (12) is moved along the oblique slide-way (45) and the rotation movement is stopped when the sliding lug (12) meets the internal edge (46). The sliding lug (12) is now positioned in a groove (D) which is the groove in which the sliding lug is located in the releasing and injection phase, the groove having a depth which will allow the ball (13) to be released from the circumferential groove (25) of the powder chamber (24). During the injection phase the sliding lug (12) moves along the groove (D) where it will reach its final position if the injector is not to be re-used. To dismount the front cover (20) the cover is rotated one step further whereby the sliding lug (12) passes below the edge (46) and into the groove (A'), being displaced 180° in relation to groove (A). In this position the front cover can be dismounted from the guide sleeve (2) since the locking lugs (21) will be free from the pins (10).

The advantage of the automatic two-chamber injector hereinabove described is that the injector is better suited to separately housing acidic and chemically aggressive substances in the chambers thereof due to the enhanced chemical resistance of the membrane as compared to an aluminium membrane as hitherto proposed and further that the membrane is able to be moved from its partitioning position to a non-partitioning position by peeling of the membrane away from the powder chamber.

In the exemplary embodiment hereinabove described with reference to the accompanying Figures of drawings the barrier material for the membrane is polychlorotrifluoroethylene. In accordance with the present invention, however, the following other materials could instead be used as the barrier material for the membrane:

a copolymer of polychlorotrifluoroethylene or a blended polymer comprising polychlorotrifluoroethylene or a copolymer of polychlorotrifluoroethylene polyvinylidene chloride, a copolymer of polyvinylidene chloride or a blended polymer comprising polyvinylidene chloride or a copolymer of polyvinylidene chloride, or a silicon oxide, for example supported in polyethylene terephthalate.

These barrier materials would also provide a membrane with the requisite impermeability properties and the advantageous improved chemical resistance to acid environments and chemically aggressive substances as compared to the previously proposed barrier material aluminium.

It should be pointed out at this juncture that although the invention has been described hereinabove with reference to an automatic two-chamber injector the present invention is applicable to the field of drug delivery devices in general. It should further be pointed out that it is not an essential requirement of the invention for the membrane to be of a laminate construction, although manufacturing and mounting advantages accrue from such a construction especially in the case of the injectors of the type hereinabove described with reference to the accompanying Figures of drawings. A skilled reader in the art will readily conceive of alternative membrane constructions.

Where, however, the membrane is to be in the form of a laminate construction for welding to a first chamber of a drug delivery device so as to partition the first chamber from a second chamber of the device, the following general layer arrangements may be mentioned:

polyethylene terephthalate layer/barrier layer/welding layer polyethylene terephthalate layer/barrier material layer/ polyethylene terephthalate layer/welding layer barrier layer/polyethylene terephthalate layer/welding layer barrier layer/welding layer Regarding the welding layer of the membrane, the material for this layer will be selected on the basis of the material forming the first chamber of the drug delivery device. Examples of possible material combinations are given in the Table below.

|  | Material of Chamber | | |
|---|---|---|---|
| Welding material | PP | PP copolymer | PE* |
| PP paint/lacquer | X | X |  |
| PE* paint/lacquer | X | X | X |
| PE* | X | X | X |
| PE* + EBA | X | X | X |
| PE* + EVA | X | X | X |
| PE* + BA | X | X | X |
| PE* + PB | X | X | X |
| PP + BA | X | X |  |
| Cellulose based polymer | X | X | X |

*By "PE" is meant a polyethylene based material which is to be taken as including the various homopolymer forms thereof, e.g. high density polyethylene, medium density polyethylene, low density polyethylene and linear low density polyethylene, cross-linked polyethylene, polyethylene ionomers such as Surlyn ® and copolymers and blends of the aforementioned polyethylenes.

The expression "paint/lacquer" in the above table means that the welding material is painted or extruded onto the underlying surface of the membrane construction in dissolved form, allowed to dry and then heated to the melting point for welding to the chamber.

In the case of the membrane being of a laminate construction for use in an injector of the type hereinabove described with reference to the accompanying Figures of drawings, the welding material and powder chamber material combinations given in the Table above result in the membrane being displaceable to the non-partitioning disposition by peeling of the membrane off the chamber.

It is to be noted that while the membrane has been described hereinabove with reference to the accompanying Figures of drawings as being welded to a powder chamber it will be clear that the membrane could of course be welded to a liquid chamber of a drug delivery device instead.

What is claimed is:

1. An automatic two-chamber injector for delivery of a drug which comprises a mixture of a lint substance and a second substance, the device comprising a barrel having a first end with a receiving portion for an injection needle and a second end with a slideable plunger, the barrel comprising a first chamber which houses the first substance, a second chamber which houses the second substance, a peelable membrane which in a first disposition thereof is welded to a surface of the first chamber so as to close the first chamber off from the second chamber to prevent mixture of the first and second substance; the membrane having a laminate structure, and a mechanism operable to displace the membrane from the first disposition to a second disposition in which the first and second substances are able to be mixed, wherein the laminate structure of the membrane comprises:

a barrier material comprising a polymer selected from the group consisting of polychlorotrifluoroethylene, a copolymer of polychlorotrifluoroethylene, polyvinylidene chloride, a copolymer of polyvinlylidene chloride, and a silicon oxide;

an outer layer comprising a material through which the membrane is welded to the surface of the first chamber, wherein the outer layer of the membrane and at least the surface of the first chamber to which the outer layer is welded are respectively formed of materials which provide a weld joint there between; and a first layer of a polyester material arranged between the barrier material and the outer layer, wherein said weld joint is of a strength which enables the membrane to be brought to the second disposition by peeling of the membrane off the first chamber, and further wherein the mechanism is adapted in use to cause the membrane to be displaced from the first disposition to the second disposition by peeling of the membrane off the first chamber.

2. The automatic two-chamber injector according to claim 1, wherein the outer layer is formed of a polyethylene based polymer or a cellulose based polymer and wherein at least the surface of the first chamber is formed of polypropylene or a copolymer thereof or of a polyethylene based polymer.

3. The automatic two-chamber injector according to claim 1, wherein the outer layer of the membrane is formed of a polyethylene based polymer and wherein at least the surface of the first chamber is formed of polyethylene or high density polyethylene.

4. The automatic two-chamber injector according to claim 1, wherein the outer layer is formed of polypropylene or a blend of polypropylene and butyl acrylate and wherein at least the surface of the first chamber is formed of polypropylene or a copolymer thereof.

5. The automatic two-chamber injector according to any one of claims 1, 2, 3 or 4, wherein the laminate structure further comprises a barrier layer containing the barrier material and the first layer of a polyester material is mounted onto one of the major surfaces of the barrier layer.

6. The automatic two-chamber injector according to claim 5, wherein the polyester layer is a first polyester layer and wherein the laminate structure comprises a second layer of a polyester material which is mounted to the major surface of the barrier layer opposite to that on which the first polyester layer is mounted.

7. The automatic two-chamber injector according to claim 6, wherein the second layer of a polyester material is polyethylene terephthalate.

8. The automatic two-chamber injector according to claim 5, wherein the first layer of a polyester material spaces the barrier layer from the outer layer.

9. The automatic two-chamber injector according to any one of claims 1, 2, 3 or 4, wherein at least one layer of the laminate structure of the membrane contains a barrier material comprising a silicone oxide, the silicon oxide comprising a supporting matrix material.

10. The automatic two-chamber injector according to claim 9, wherein the matrix material is formed of polyethylene terephthalate.

11. The automatic two-chamber injector according to claim 9 wherein the silicon oxide is silicon dioxide.

12. The automatic two-chamber injector according to claim 2 or 3, wherein the outer layer is formed of a blend of polyethylene with ethylene-vinyl acetate, ethylene-butylacrylate, polybutylene or butyl acrylate, a cross-linked polyethylene or a polyethylene ionomer.

13. The automatic two-chamber injector according to claims 2 or 3, wherein the first chamber is formed substantially exclusively of the polyethylene based polymer.

14. The automatic two-chamber injector according to claim 1, wherein the first layer of a polyester material is polyethylene terephthalate.

* * * * *

UNITED STATES PATENT AND TRADEMARK OFFICE
CERTIFICATE OF CORRECTION

PATENT NO. : 6,387,074 B1
DATED : May 14, 2002
INVENTOR(S) : Horppu et al.

It is certified that error appears in the above-identified patent and that said Letters Patent is hereby corrected as shown below:

<u>Title page,</u>
Item [86], both the §371 and §102(e) date is -- Feb. 18, 1998 --.

Item [56], References Cited, add the following documents:
-- GB 2,139,634, published 1/84;
GB 2,119,741, published 11/83;
WO 97/42897, published 11/97; and
EP 288,443, published 10/88 --.

<u>Column 11,</u>
Line 47, delete "lint" and substitute therefore -- first --.

Signed and Sealed this

Twenty-fourth Day of December, 2002

JAMES E. ROGAN
*Director of the United States Patent and Trademark Office*